United States Patent [19]
McFarlane

[11] 3,957,054
[45] May 18, 1976

[54] SURGICAL DRAINAGE TUBE
[76] Inventor: Richard H. McFarlane, c/o Coilform Company, 2571 Kaneville Court, Geneva, Ill. 60134
[22] Filed: May 1, 1975
[21] Appl. No.: 573,771

Related U.S. Application Data
[63] Continuation of Ser. No. 401,051, Sept. 26, 1973, abandoned.

[52] U.S. Cl............................................ 128/350 R
[51] Int. Cl.$^2$........................................ A61M 27/00
[58] Field of Search.............................. 128/350 R

[56] References Cited
UNITED STATES PATENTS
3,430,631  3/1969  Abramson................... 128/350 R OTHER PUBLICATIONS
Jackson, Frederick E. et al., "Jackson–Pratt Brain Drain", IN International Surgery, 57$^8$: 658–659, 1972.
"Beneventi Tubing", IN American Cystoscope Makers, Inc. Catalog of Catheters and Accessories, 1960, p. 63.

Primary Examiner—Channing L. Pace

[57] ABSTRACT
As an article of manufacture an improved drain tube which is flexible and pliable for use after surgical operations and which includes a plurality of ribs arranged in such a fashion about the interior of the column of the tube so that the tube cannot be collapsed and which at all times promotes drainage of body fluids as healing occurs.

4 Claims, 5 Drawing Figures

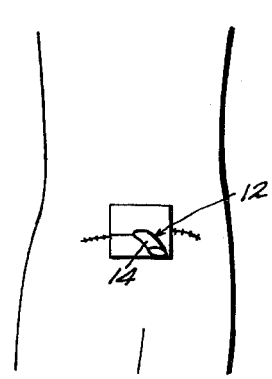
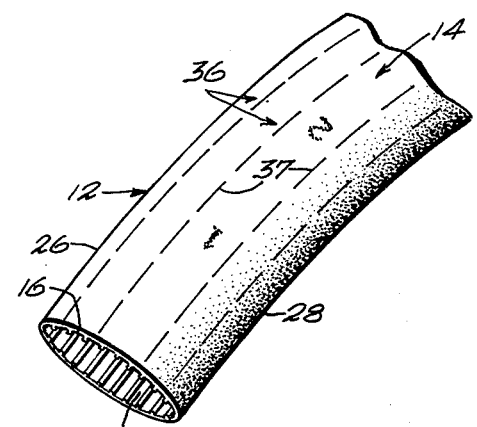
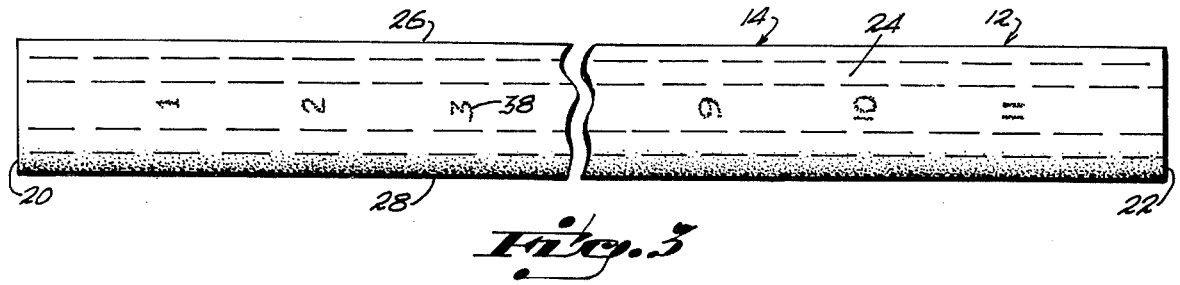
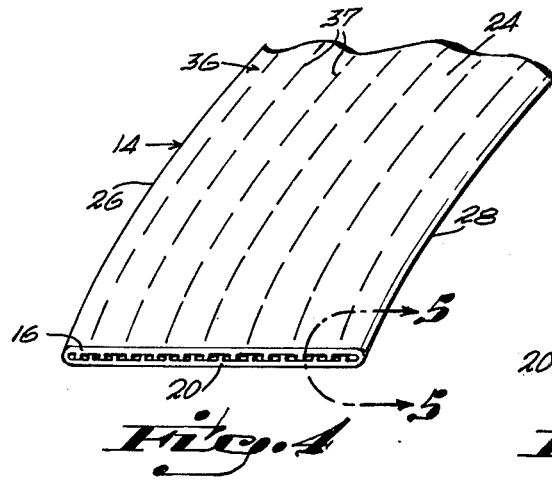
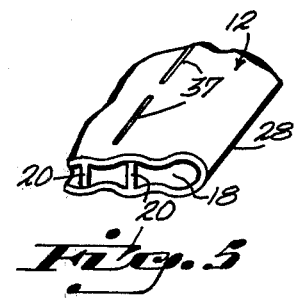

SURGICAL DRAINAGE TUBE

This application is a continuation of application Ser. No. 401,051 filed Sept. 26, 1973, and now abandoned.

FIELD OF THE INVENTION

This invention relates to a surgical drain.

BACKGROUND OF THE INVENTION

As is perhaps well known, tubular surgical drains used in draining after an abdominal surgery have presented a long outstanding problem of effectiveness of drainage versus comfort of the wearer. Mechanically, the problem has been that tubular drains, if thin walled so as to be pliable and, therefore, more comfortable, collapse under body pressures and forces exerted upon them or at the surgical cut as the healing process occurs with swelling and, later, as the swelling goes down, the inside surfaces of such tubes tending to stick together or, become kinked and blocked so that drainage is not effected at the desired rate. On the other hand, if the tubular length is more rigid or reinforced the tube is uncomfortably situated in an area which is sore and painful because of the operation. The problem has been approached as in U.S. Pat. No. 1,596,754 to Moschelle, dated 1926 by providing reinforcing ribs to prevent collapse of the tube, the ribs being longitudinally extending and being circumferentially thick and with sides which do not extend perpendicularly from the tube wall so as to be relatively thick at the rib base, as in the round tube with thick ribs, as in the round tube with a thick rib in which a longitudinal passageway which never collapses because of thick walls is defined and in which thick spiral ribs may be provided. Such thick ribs have proven to be uncomfortable. Representative later efforts are illustrated (a) by the patent dated in 1963 to Coburn, U.S. Pat. No. 3,112,746, which utilizes a tube of smaller diameter within the column of a larger diameter tube, and (b) the patent dated 1969 to Abramson, which utilizes relatively rigid tubular stock within an outer more pliable tube.

Generally, it is seen that the art is confronted with the problem of a comfortable drain which is flexible and pliable but which, nevertheless, does not collapse so as to remain open for drainage.

PRESENT INVENTION GENERALLY

It has been found that drainage takes place along the surface of a drainage tube, both the interior and the exterior surfaces and that it is preferred that a tube for drainage purposes not collapse and have a relatively large surface over which body fluids may drain from a wound. The present invention provides a structure which is flexible and pliable and therefore comfortable but which, nevertheless, is so constructed as to not collapse to a completely closed condition but, rather, to a condition in which there are a plurality of capillary tubes and promotion of body fluid flow takes place under all conditions when in use.

It is, accordingly, an object of this invention to provide an inexpensive, flexible, pliable drainage tube which is comfortable in use, does not collapse, and when in an extreme condition of external forces being applied thereto, nevertheless, defines a plurality of capillary tubes, a relatively high surface area so as to promote drainage flow by capillary type action and for movement of material being drained over, under and around the surfaces of the tube, both exterior and interior.

It is another object of this invention to provide a new improved, inexpensive surgical drain which provides indicia to guide a surgeon in withdrawal of the tube in progressive steps from the wound as it heals.

DESCRIPTION OF THE DRAWINGS

FIG. 1 is a perspective view of the instant invention illustrating the same in use;

FIG. 2 is an enlarged perspective view of one end of the surgical drain shown in FIG. 1;

FIG. 3 is a partial view of the drain;

FIG. 4 is a partial perspective view of the drain in a fully collapsed and extreme condition; and FIG. 5 is an enlarged view of that portion of FIG. 4 with the arrowed lines 5—5 therearound.

DETAILED DESCRIPTION OF A PREFERRED EMBODIMENT

Referring to the drawings wherein like reference characters designate like or corresponding parts throughout the several views and referring particularly to FIG. 1, the surgical drain 12 comprises a tubular length 14 characterized by a thin continuous wall 16 of flexible pliable medical grade rubbery material defining a collapsible column or passageway 18 which extends between a first end and a second end 20 and 22. The exterior surface 24 of the length is substantially smooth and uniform throughout its surface length.

Referring to FIG. 2, the normal cross section is generally flat, being somewhat opened so as to define a slightly oval cross section throughout its length in a normal condition, the thin wall being such that the weight of the tube when on a flat surface is sufficient to deform the longitudinally extending edges 26 and 28 which are parallel to the longitudinal centerline so as to form a bend of a relatively short radius of coverage.

Within the column 18 a plurality of longitudinally extending ribs 20 are provided which extend continuously longitudinally between the ends. The ribs are integral with the tube length and of the same flexible pliable, rubbery medical grade material in the preferred embodiment. Preferably the ribs are of a circumferential thickness the same as or slightly less than the thickness of the wall and are equally spaced about the column. Also, in the preferred embodiment the ribs extend a common distance into the column of the tube and preferably the distance is about equal to the thickness of the tube wall, so as to be yieldable but not readily collapsible, that is so as to be short and stubby so as not to collapse capillary tubes defined between the ribs and confronting surfaces of the interior wall of the tube as will now be described with reference to FIG. 4. The space between the ribs is at least twice as great as the circumferential thickness of the ribs in the illustrated embodiment so that, when the tube is collapsed by a circumferentially applied inwardly directed force, such as at surgical cut zone, there are formed a plurality of generally parallel capillary tubes in the interior of the column and, externally, the exterior surface of the tube, between the ribs is slightly deformed so as not to interfere with exterior movement of material flowing along the exterior surface of the tube.

Preferably, longitudinally extending lines of slits are provided through the wall of the tube closely adjacent but not at the line of juncture of the ribs to the wall of the tube, the lines being designated by the numeral 36 and the individual slits being designated by the numeral 37, these slits permitting flow of material at an obstructed zone along flow paths which can extend interiorly and then on the exterior surface and then interiorly wending their way along the surfaces of the tube for continuous drainage irrespective of the adjustment of the body of a person on whom the tube is positioned.

Also, in the preferred embodiment along the length of the tube a plurality or series of guide marks 38, see FIG. 3, are provided in descending order from the first or proximal end 22 of the tube so that the amount of tube remaining in the body may be readily determined and the tube may be advanced in successive increments of predetermined length as the healing process occurs. In a preferred embodiment, these marks are vacuum formed so as to provide a relatively smooth surface without sharp edges and which are, nevertheless, readily discernible. The series are also provided in the central zone intermediate the longitudinal extending edges 26 and 28.

The rubbery material preferably is radio opaque so as to be visible by X-ray techniques. This may be achieved by the addition of a barium compound in the rubbery material before extrusion of it. The material used is of medical grade and preferably has a hardness which is compatible with the hardness of the skin of a person in the abdominal area.

In a preferred embodiment the wall thickness of the tubular stock is in the order of about 0.005 to 0.020 inches.

It is thus seen that this invention provides an improved flexible pliable drainage tube, such as is commonly known as a Penrose drain, which can be comfortably tolerated by an individual following operation for a period of time over which the healing process takes place and which does not include rigid and, therefore, painful reinforcing portions to a wearer and which is adapted to be readily advanced in successive stages as healing takes place with the flow at all times being encouraged by the structure of the tube described above, the flow being over the surface of the tube on both the interior and the exterior surfaces which are accessible to flow paths in response to changes in pressures exerted upon the tube and which employs capillary type flow when in an extreme collapsed condition.

What is claimed is:

1. As an article of manufacture, a surgical drain for a wound comprising a length of flexible, pliable, rubbery, medical grade material which is radio opaque defining a thin tubular wall having a first end to be inserted through the wound into a human body and extended with the second end extending out of the wound, said wall having a cylindrical, smooth, exterior surface and a collapsible passageway therethrough which is normally of oval cross section and is adapted to be flattened in response to externally applied surface pressure, so as to be substantially flat, said tubular wall having a plurality of flexible, pliable laterally yieldable longitudinally ribs of rubbery material along the length thereof and extending depthwise into said passageway whereby, when said length is used as a drain, said passageway is not collapsed into a completely closed condition by normal pressures within the body, said ribs being equi-spaced about said passageway and extending into said passageway so that, when a radially inwardly directed force is exerted upon the exterior surface of said tubular wall, the wall will collapse with the terminal ends of the ribs of rubbery material engaging the confronting interior surface of the tube so as to define a plurality of adjacent yieldable internal capillary passageways, said tube length being of uniform cross section throughout the length thereof between said ends and said ribs being integral with said tubular wall, and said ribs extend into said passageway a substantially common distance in perpendicular relation to the tubular wall and said surfaces of said ribs extending into said passageway are substantially parallel to one another.

2. The article as set forth in claim 1 wherein the circumferential thickness of said ribs is substantially equal to the thickness of said tubular length.

3. The device as set forth in claim 1 wherein indicia marks are provided on the exterior surface of said tubular wall at equi-spaced points therealong adjacent one end to measure the distance between said one end and the indicia marks.

4. The device as set forth in claim 1 wherein a plurality of longitudinally extending interrupted lines of slits are provided through the wall of the tube so that material may flow both along the interior and exterior surface of said tubular wall.

* * * * *